United States Patent [19]

Lindemann et al.

[11] Patent Number: 4,878,906
[45] Date of Patent: Nov. 7, 1989

[54] ENDOPROSTHESIS FOR REPAIRING A DAMAGED VESSEL

[75] Inventors: Peer Lindemann, West Bend; Victor M. Haughton, Dousman, both of Wis.

[73] Assignee: Servetus Partnership, Milwaukee, Wis.

[21] Appl. No.: 202,562

[22] Filed: Jun. 6, 1988

Related U.S. Application Data

[62] Division of Ser. No. 843,992, Mar. 25, 1986, abandoned.

[51] Int. Cl.[4] .......................... A61F 2/06; A61B 17/04
[52] U.S. Cl. ..................................... 623/1; 128/334 R
[58] Field of Search ............... 623/1, 12, 66; 128/303, 128/11, 325, 334 R, 341, 343, 344; 604/96, 101, 104; 600/36

[56] References Cited

U.S. PATENT DOCUMENTS 3,657,744  4/1972  Ersek .
4,140,126  2/1979  Choudhury ......................... 623/1 X
4,425,908  1/1984  Simon .
4,512,338  4/1985  Balko et al. ......................... 128/341
4,562,596  1/1986  Kornberg .
4,577,631  3/1986  Kreamer ............................. 623/1 X
4,617,932  10/1986 Kornberg ........................... 623/66 X
4,733,665  3/1988  Palmaz ............................... 604/96 X Primary Examiner—Alan W. Cannon
Attorney, Agent, or Firm—Andrus, Sceales, Starke & Sawall

[57] ABSTRACT

A prosthesis consisting of a flexible thin-walled sleeve for reinforcing and repairing a damaged vessel and a process of placing the flexible sleeve in the vessel by collapsing the sleeve radially onto an expandable and contractable member and encasing the member and sleeve in a sheath; and then sliding the sleeve in place in a vessel covering the damaged area of the vessel and removing the sheath; then expanding the expandable member and the sleeve so that the sleeve covers the damaged area and forms a sealed interface on its outer peripheral ends with the inner peripheral surface of the vessel to thereby provide a bridging passage across the damaged area in the vessel. The device provides a process to reinforce or repair weakened, damaged, narrowed blood vessels or to divert flow in branching vessels. The sleeve is a flexible, plastic, thin-walled sleeve molded with various types of ribs and reinforcements to be used as an endovascular prosthesis. It also includes a means of delivering the prosthesis to the damaged blood vessel without surgery. With the device a physician may patch the inside of a blood vessel without performing an arteriotomy and without the use of an operating room and other facilities. A patch is placed within a vessel endovascularly preventing further expansion of the blood vessel, preventing leakage of the blood from the vessel wall and preventing or treating narrowing of the blood vessel, eliminating blood flow into a branching vessel from the abnormal region.

4 Claims, 4 Drawing Sheets

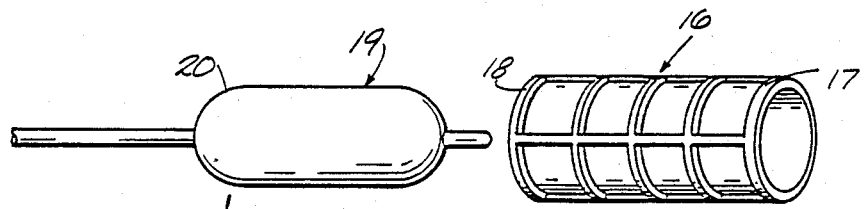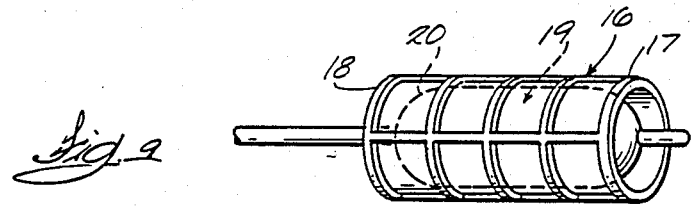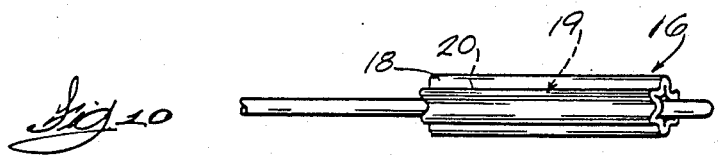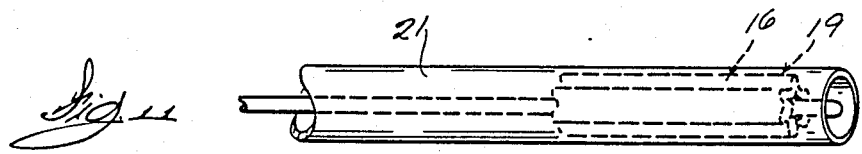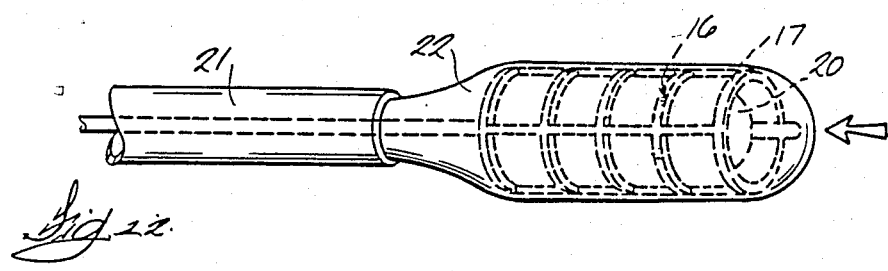

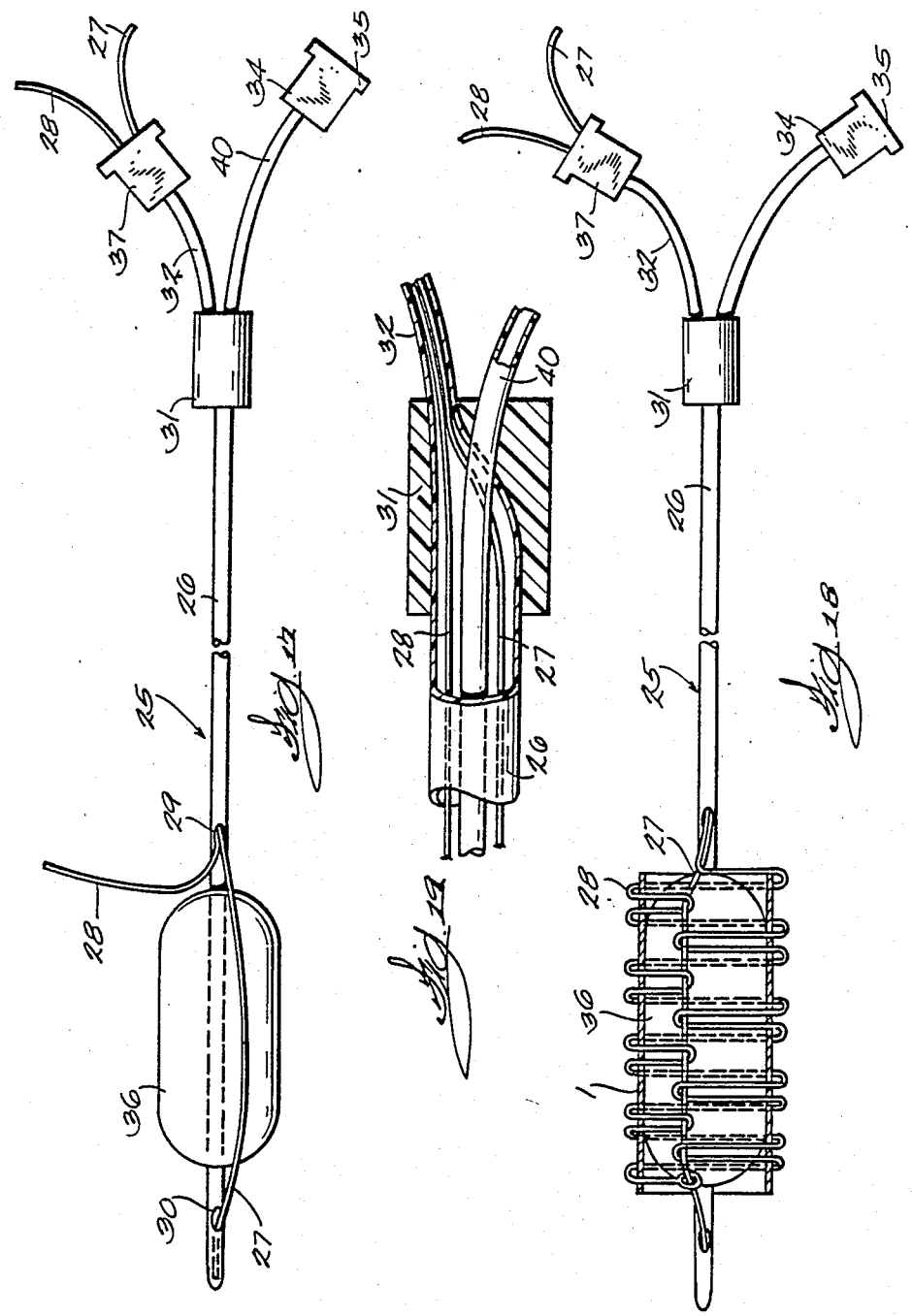

ENDOPROSTHESIS FOR REPAIRING A DAMAGED VESSEL

This is a division of application Ser. No. 06/843,993, filed Mar. 25, 1986 now abandoned.

BACKGROUND AND SUMMARY

This invention relates to a means of treating a damaged vessel in a body and, more particularly, to providing a flexible thin-walled sleeve and a method of inserting the sleeve into the damaged vessel, expanding it against undamaged walls to form a sealed interface to provide a new bridging passage across the damaged area.

The invention deals with a means of treating a blood vessel with defects without expensive and complex surgery. The device can be used for treatment of congenital malformations or for the treatment of acquired abnormalities such as traumatic aneurysms or for therapeutic occlusion of vessels.

Traumatic injuries to blood vessels commonly consist of rupture of the vessel with the formation of hematoma around the vessel, which becomes as it liquifies a pseudoaneurysm without a defined vascular wall. The treatment of these by surgery is often difficult because severe bleeding is encountered as the pseudoaneurysm is explored. Maintaining the patency of the vessel while sealing the leak may be difficult. With the invention the wall may be patched from the inside, preventing further bleeding.

A second type of traumatic injury is a dissection. In this process a partial tear of the vessel is formed so that blood collects between the layers of the vessel wall. The collection of blood eventually narrows the vessel lumen. Surgical repair may be difficult. With the invention, a prosthesis may be placed within the blood vessel without surgery to restore patency to the blood vessel lumen and to prevent further blood from accumulating in the vessel walls.

Aneurysm is another type of vascular problem for which this invention is intended. An aneurysm consists usually of a weakened blood vessel wall which, when exposed to the pressure of circulating arterial blood, expands and in some cases ruptures. Surgical treatment involves complicated and diverse procedures to reinforce the blood vessel wall and to clamp the aneurysm or the vessel from which it originates; or in some cases to occlude the vessel. With the invention, an endoprosthesis is placed so that the vessel wall is reinforced from within and blood is prevented from entering the aneurysm. The result is that the aneurysm thromboses and fibroses thereby ceasing to present a risk to the patient. The patency of the vessel is preserved.

In a fistula there is an anomalous or acquired connection between a vessel containing blood under high pressure such as an artery with a vessel under lower pressure such as a vein. Because of the differences of pressure, blood flows swiftly from the arterial to the venous channel with, in most cases, reduction of the flow to the tissues normally supplied by the artery. To restore normal blood flow, and sometimes to control the abnormal cardiac output, surgical procedures have been devised for treating the fistulae. With the invention, a prosthesis may be place in the artery so that the blood flow is conducted only through the artery and excluded from the fistula. The process includes a way in which this can be done without complex surgery.

Atherosclerosis is a common disease of the blood vessels for which many different types of treatment have been devised. Atherosclerotic narrowing of the blood vessels is often an indication for surgery when the circulation is impeded. Atherosclerotic disease without significant narrowing of a blood vessel may also be an indication for surgery because the roughened vessel wall creates thrombi which detach and enter the blood flow and cause significant complications. Endarterectomy is one type of surgery for these lesions. Recently transluminal angioplasty has been developed as a way of treating these lesions. Surgery is expensive, complicated, and has significant morbidity. Transluminal angioplasty has a significant failure rate and a risk of detaching fatty or thrombus material into the bloodstream, causing complications when they embolize. The invention provides for an alternative to transluminal angioplasty and surgery. The product is placed within the blood vessel. The invention also includes a technique which permits the blood vessel to be dilated with the endoprosthesis in place, restoring the normal diameter of the lumen, while preventing atherosclerotic material from embolizing.

There are numerous other diverse diseases of blood vessels which could be treated by the invention. One example is fibromuscular hyperplasia. In this disease there are numerous bands or constrictions within the vessel limiting the blood flow. With the invention the vessel can be dilated and a new surface created on the inside of the vessel.

The list of indications is not complete or all inclusive, nor is the invention limited to blood vessels. Any hollow body structure could potentially be treated with the invention, nonsurgically, or with reduced surgery. For example, the invention could be used to restore the patency of a ureter, urethra, bile duct, or any body vessel which has been narrowed, weakened, or in any other way requires reinforcement. In some of these applications, valves will be included in the endoprosthesis. A prosthesis with a one-way valve may be used in a ureter to prevent reflux of urine from the bladder, for example. Other body channels include esophagus, bile ducts, urethra, thrachea, enterostomies, and the like. In some of these applications, flanges are included in the prosthesis.

Accordingly, applicants have provided means whereby surgery may be eliminated by simply inserting the prosthesis in the vessel to provide a bridging of the passage and normal circulation in the body.

It is an object of this invention to provide an endoprosthesis for use in a damaged vessel which provides a smooth inner surface and reinforced walls bridging the damaged portion of the vessel.

It is another object of this invention to provide an endoprosthesis consisting of a flexible, thin-walled sleeve for use in repairing the damaged vessel. Either a porous or non-porous prosthesis may be used depending on the nutritional requirements of the blood vessel.

It is a further object of this invention to provide a method of placing a prosthesis consisting of a flexible thin-walled sleeve in a damaged vessel of the body to restore normal flow through the passage.

It is a further object of this invention to provide a method and an apparatus for inserting the prosthesis in a damaged vessel. The method consists of radially collapsing the flexible, thin-walled sleeve for reception in a sheath so that the sleeve may be transported through a vessel to the damaged area in the vessel. Withdrawing the sheath allows the radial expansion of the sleeve to form a bonding interface with the walls of the vessel and thereby provide a renewed surface and passage bridging the damaged area of the vessel.

The objects of the invention are accomplished with a prosthesis and a technique for delivering it to a damaged vessel. The prosthesis is a plastic sleeve which has been molded to fit the interior surface of the blood vessel. The sleeve may have various shapes and forms depending on the indication for treatment of the vessels in which it will be used. The inside diameter of the prosthesis is operated to match the normal inside diameter of the vessel to be treated so that the normal premorbid diameter is restored. Ribs, struts, elastics, fabrics, fasteners, or other design characteristics may be included in the prosthesis wall during the molding process to give it specific qualities for a therapeutic indication. In some cases a hollow straight cylinder will be molded, and in other cases a curved cylinder, and in others a y-shaped configuration will be molded. The surfaces of the sleeve will be smooth or textured and the lumen may be uniform or tapered.

The technique for delivering the sleeve to the damaged vessel is essentially a process of radially collapsing the sleeve on a contractable and expandable member. In the contracted condition, the sleeve and the expandable member are transferred to the inside of a sheath. The sheath, the sleeve and the expandable member are then transferred to the inside of the vessel. Withdrawing the sleeve slightly allows the expandable member to expand the sleeve to form a sealing interface between the peripheral outer surface of the two ends of the sleeve and bridge the damaged area of the vessel and thereby provide a new passage in the vessel. The expandable member and sheath are then withdrawn from the vessel and the process is completed.

BRIEF DESCRIPTION OF THE DRAWINGS

Referring to the drawings:

FIG. 8 illustrates a balloon catheter axially designed with the flexible thin-walled sleeve;

FIG. 9 illustrates the balloon catheter disposed within the sleeve.

FIG. 10 illustrates a flexible thin-walled sleeve and the balloon catheter collapsed radially;

FIG. 11 illustrates the flexible thin-walled sleeve collapsed on the balloon catheter and axially received within a sheath;

FIG. 12 illustrates a means of constricting the flexible thin-walled sleeve to force it to a smaller diameter as it is moved axially to the left and then received within the sheath;

FIG. 17 illustrates a catheter with an inflatable portion for expanding a flexible thin-walled sleeve and also a wire and thread which may be used to constrict the flexible thin-walled sleeve when the balloon catheter portion is collapsed;

FIG. 18 illustrates a catheter with a balloon in which the thread is wrapped around the flexible thin-walled sleeve to constrict it to a smaller diameter and fastened to a wire which is removably secured in the catheter. The wire provides a means for releasing the thread and allowing the flexible thin-walled sleeve to expand to its normal radial diameter when it is positioned in the vessel.

FIG. 19 illustrates an enlarged view of the junction box shown in FIGS. 17 and 18.

DETAILED DESCRIPTION OF THE PREFERRED EMBODIMENT

FIGS. 1 through 7 illustrates various modifications of a flexible thin-walled sleeve used as a prosthesis in this invention.

Figure 1:
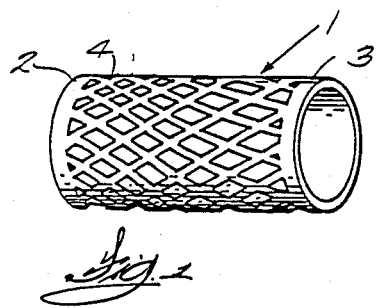
FIG. 1 illustrates a prosthesis consisting of a flexible thin-walled sleeve having diagonal reinforcing ribs.
Figure 2:
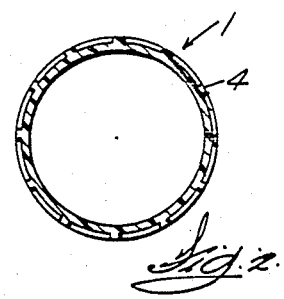
FIG. 2 is a cross section view taken on the prosthesis of FIG. 1.

FIGS. 1 and 2 illustrate a sleeve in which the reinforcing ribs run diagonally across the outer surface of the sleeve. The inner periphery of the sleeve is a smooth surface to allow a laminar flow of the fluid within the sleeve. Each end of the sleeve 1 is formed with an outer peripheral surface 2 and 3 which engage the inner surface of the vessel to form a sealed interface between the sleeve and the vessel. The diagonal ribs 4 provide sufficient stiffness to the sleeve such that it retains its shape and forms the sealed interface with the vessel.

Figure 3:
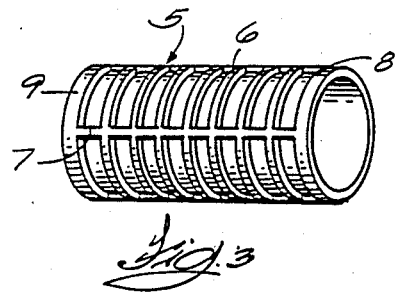
FIG. 3 is a flexible thin-walled sleeve having circumferential and axial reinforcing ribs.

FIG. 3 illustrates a sleeve 5 which has circumferential ribs 6 and longitudinal axial ribs 7. This sleeve also has peripheral end surfaces 8 and 9 which engage the inner surface of the vessel to provide a sealed interface.

Figure 4:
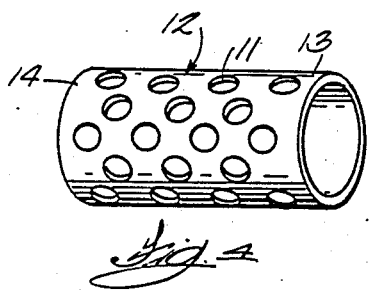
FIG. 4 is a flexible thin-walled sleeve having recesses to provide reinforcement of the sleeve.

FIG. 4 illustrates a modification of the invention in which recesses 11 are formed in the sleeve 12. The recesses in the outer surface reinforce the sleeve and provide a degree of stiffness in which it will press the peripheral end surfaces 13 and 14 to form sealed inner surfaces with the vessel in which it is received.

Figure 5:
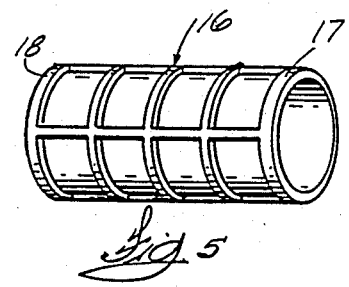
FIG. 5 is a flexible thin-walled sleeve having circumferential and axial reinforcing ribs.

FIG. 5 illustrates a sleeve 16 with circumferential and axial ribs on the outer surfaces of the sleeve, similar to other sleeves but with somewhat larger reinforcing ribs than shown in FIG. 3. The inner periphery is smooth to allow laminar flow internally. The sleeve 16 also has peripheral outer end surfaces 17 and 18 to form sealed interfaces with the vessel in which it is received.

Figure 6:
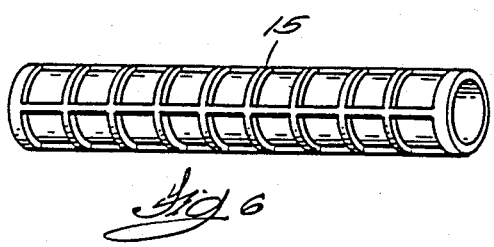
FIG. 6 is a longer and smaller flexible thin-walled sleeve having circumferential and longitudinal reinforcing ribs and also showing the end sealing surfaces for engaging the walls of the vessel which receives the sleeve.

FIG. 6 illustrates a sleeve 15 which may be constructed basically the same as in FIGS. 1, 2 or 4, and has the reinforcing ribs and end surfaces needed to provide a degree of stiffness in the sleeve, although the sleeve is also a thin-walled flexible sleeve.

Figure 7:
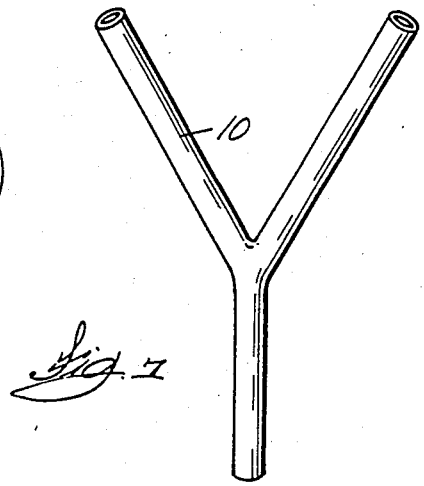
FIG. 7 is an illustration of a flexible thin-walled sleeve having branched passages connecting to the main passage of the sleeve.

FIG. 7 illustrates a configuration for reception in a vein or artery in which there is a branch of the artery. The reinforcing ribs may also be formed on this modification and also the sealing surfaces are provided on the ends of each of the tubular sections. The Y-configuration of the sleeve 10 might be inserted in this shape or three sections could be inserted, depending on the injury to the vein.

FIG. 8 illustrates a sleeve 16 axially aligned with a balloon catheter 19. The balloon 20 is usually partially inflated and then inserted within the central opening of the sleeve to a position shown in FIG. 9. The balloon of the balloon catheter 19 is then expanded to fill the central opening of the sleeve 16.

FIG. 10 illustrates the sleeve 16 collapsed around the deflated balloon to position it in the thin-walled sheath 21 as shown in FIG. 11.

FIG. 12 illustrates a manner in which the sleeve 16 can be contracted around the deflated balloon as the sleeve 16 is collapsed within the tapered sleeve 22 and received within the thin-walled sheath 21. The sheath 21 receives the collapsed sleeve 16 and the deflated balloon 20 in the position shown in FIG. 11. In this position the thin-walled sheath 21 and the balloon catheter 19 are ready to be inserted in the vessel.

Figure 13:
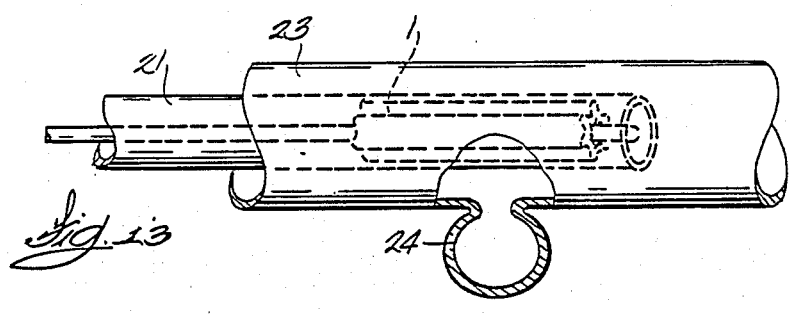
FIG. 13 illustrates the flexible thin-walled sleeve collapsed within the sheath and then transferred to the position inside a vessel which has an aneurysm.

FIG. 13 illustrates the vessel 23 with an aneurysm 24. The aneurysm is some form of a rupture that may be caused by shock or accident or injury of some kind or by disease. The aneurysm is to be repaired or treated by covering the vessel with a thin-walled flexible sleeve. The thin-walled sheath 21 carrying the flexible sleeve 16 and the deflated balloon of the balloon catheter 19 are shown positioned within the vessel to bridge the aneurysm.

Figure 14:
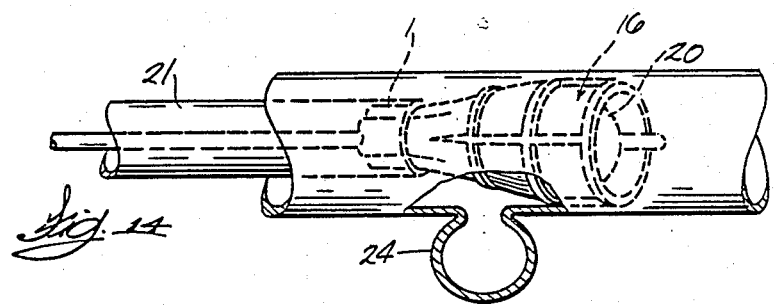
FIG. 14 shows the withdrawing of the sheath and the expansion of the balloon catheter to force the flexible thin-walled sleeve against the inner surface of the vessel.
Figure 15:
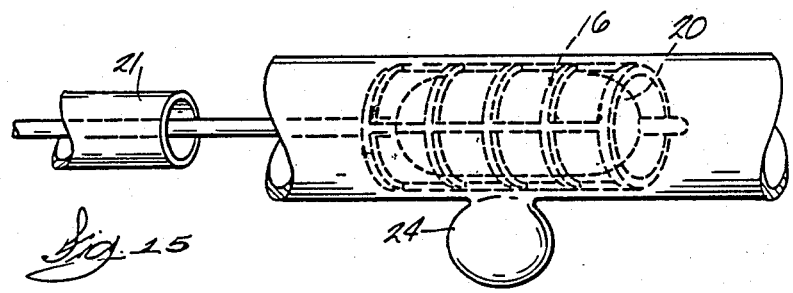
FIG. 15 illustrates the completed withdrawal of the sheath and the expansion of the balloon catheter to force the flexible thin-walled sleeve against the inner surface of the vessel to from a sealed interface between the flexible thin-walled sleeve and the peripheral inner surface of the vessel.
Figure 16:
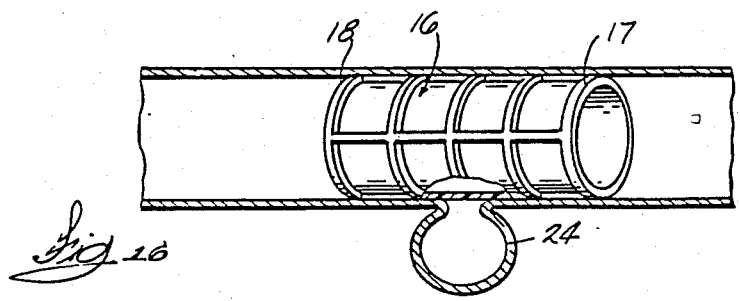
FIG. 16 illustrates the flexible thin-walled sleeve in position within the vessel bridging the aneurysm and forming renewed passage.

The thin-walled sheath 21 then is partially withdrawn, as shown in FIG. 14. Simultaneously the balloon 20 of the balloon catheter 19 is partially inflated expanding the sleeve 16 against the inner wall of the vessel 23, forming a sealed interface at the end of the sleeve 16 as it engages the inner surface of the vessel 23. The sheath 21 is then completely withdrawn as shown in FIG. 15 and the balloon 20 of the balloon catheter 19 is fully inflated, expanding the sleeve 16 against the inner surface of the vessel 23. The two peripheral end surfaces of the sleeve 16 form a sealed interface with the inner wall of the vessel 23, sealing off the aneurysm 24 from the passage in the vessel 23. The balloon 20 of the balloon catheter 19 may then be moved from the sleeve 16 and the vessel 23 is repaired. The aneurysm 24 shown in FIG. 16 is sealed off from the vessel and a renewed surface is provided bridging the aneurysm to allow flow of fluid through the vessel 23.

FIG. 17 illustrates a catheter 25. The catheter 25 includes tubular structures 32 which carry a wire 27 and a thread 28. The wire 27 goes through the sleeve 26 out of the opening 29 and into the opening 30. Wire 27 is releasably fastened at the forward end of the sleeve. The thread 28 extends forwardly out of the opening 29. The junction box 31 connects the catheter 25 to the tubes 32 and 40. The tube 32 is connected to the female connector and valves 34 and 35. The connector 35 is adapted so that a syringe may be connected to allow inflation and deflation of the balloon 36. The wires 27 and thread 28 may be passed through the other female connector 37, through the tube 32, catheter 26 and openings 29 and 30.

FIG. 18 illustrates the thin-walled flexible sleeve 1 receiving the balloon 36 and the wire 27 extending through the catheter 26 out of the opening 29 and back into the opening 30 where it is fastened. The thread 28 is wrapped around the sleeve and back and forth around the wire 27 and, as it is tightened and the balloon is deflated, the sleeve 1 collapses radially to a configuration similar to that shown in FIG. 10. The catheter may then be inserted into the thin-walled sheath 21 for transfer to a position in the damaged vessel as previously described.

The molding of the thin-walled flexible sleeve which is used as a prosthesis can be performed in the following manner. The construction of the thin-walled flexible sleeve is illustrative and not limiting. A silicone, being a silicone compound fluid with fillers and curing agents, such as a catalyst, is mixed in proportion of ten parts of silicone and one part of the catalyst by weight. Each is put in a separate container and then refrigerated. Next a mold, such as aluminum, acryl-epoxy may be used which is carefully cleaned and refrigerated. When both the mold and the catalyst components reach the same temperature, approximately 10°–15° C., the silicone and the catalyst are mixed and immediately placed in a vacuum for the extraction of entrapped air pockets.

The mixed material, after the vacuum therapy, is introduced into the mold by injection. The mold and the material, consisting of the silicone and the agent, are now heated slowly to room temperature, so that the mixture will gel. Thereafter, slowly and over approximately thirty minutes, the temperature is raised to 100° C. and held for ninety minutes. This process will give a smooth surface to the molded sleeve.

The physical properties of the silicone are as follows:

| Appearance: | Flesh color or clear Smooth uniform surface | |
|---|---|---|
| Properties: | Specific gravity @ 25 c | 1.07–1.12 |
| | Durometer, shore A | 25 minimum |
| | Tensile, Die C. psi | 550 minimum |
| | Elongation, % | 350 minimum |
| | Flamability | Self extinguishing |
| | Non volatile content | 99.8 |
| | Water vapor permability g/24 hr/m$^2$/mmHg/cm thickness | 1.08 × 10$^3$ |
| Metalic Elements: | Pb, Sn, Cr, Bi, V, Ag | PPM less 10 each |
| | Co, Ni, Cu, Zr, Bb, As, | PPM less 10 each |
| | Zn, Se, Cd, Hg, Tl | PPM less 10 each |
| | Sb, Ge, Mn, Mo, | PPM max 10 each |
| | Na, Mg, Ca, | PPM max 100 each |
| | P. Ti, Fe, | PPM max 50 each |
| | Al | PPM max 200 each |

The technique claimed is a method of introducing an endovascular prosthesis into a blood vessel without surgery. The invention uses a balloon catheter, or other expandable-contractable element, a molded endoprosthesis, and a thin-walled catheter or sheath, or other device for retracting the sleeve.

Prior to performing the method, the prosthesis is molded to the appropriate diameter and configuration. Conventional clinical studies, such as angiography, computed tomography, 3-D computed tomography, MR scanning, etc. are used to determine dimensions of and specifications of the prosthesis. The balloon catheter is then placed within the endoprosthesis as shown in FIG. 9. The balloon catheter is selected so that the diameter of the balloon when inflated is the same as the inside diameter of the endoprosthesis, and the length of the balloon is approximately the same length as the endoprosthesis. For some procedures a second balloon, either proximal or distal to the one that fits inside the endoprosthesis, may be used. The balloon is inflated to fill the endoprosthesis. Then the endoprosthesis and the balloon are collapsed simultaneously, FIG. 10, either manually or with the aid of mechanical devices, so that the outside diameter of the collapsed prosthesis fits conveniently within the sheath, FIG. 11. One technique uses a thread wrapped around the sheath, FIGS. 17 and 18, in such a way that removal of a wire and the thread releases the prosthesis.

When the sheath has been loaded with the endoprosthesis and balloon catheter, the patient is brought to a fluoroscopic unit for treatment. The selective catheter is placed in the vessel to be treated, with conventional angiographic techniques. The selected catheter is placed in the vessel to be treated so that its tip is near the defective portion of the vessel FIG. 13. The sheath is introduced within the selective catheter so that the end of the sheath lies near the distal end of the weakened, defective of impaired vessel to be treated. Hydraulic pressure is then introduced into the balloon through the balloon catheter lumen. Then, the movement of the balloon catheter is prevented and the sheath is gently and slowly withdrawn, FIG. 14. As the cannula exposes the endoprosthesis to the blood vessel, the balloon begins expanding and pressing the endoprosthesis against the vessel wall. The process is continued until the entire endoprosthesis has been delivered into the vessel FIG. 15. A second balloon on the balloon catheter, which can be inflated separately, may facilitate this procedure. With the second balloon blood flow could be interrupted transiently prior to the delivery of the endoprosthesis. The procedure is executed so that the prosthesis is pushed into firm contact with the vessel wall so that any narrowing of the vessel is eliminated by dilation during the procedure. Once the endoprosthesis has been placed, the balloon catheter is deflated, withdrawn inside the sheath, then the sheath is withdrawn into the selective catheter, and the selective catheter withdrawn from the body FIG. 16.

An alternative method dispenses with the sheath. In this technique the endoprosthesis is placed around the balloon and reduced in diameter by wrapping with thread. A selective catheter is placed as in the previous technique. Then the thread is released and moved from around the prosthesis by withdrawing a wire to permit the prosthesis to assume its shape in the vessel.

There are various conventional refinements of angiographic technique which may be used in this invention. These consist of means to provide circulation of sterile saline around the sheath to prevent blood clotting, circulation of sterile saline around the endoprosthesis to facilitate its movement and prevent thrombosis. A large variety of commercial catheters, sheaths, guidewires and balloon catheters can be adapted to this procedure.

The invention also includes some ways in which handling of the endoprosthesis may be facilitated. An adhesive or lubricant may be applied to the outside of the endoprosthesis so that movement of the endoprosthesis in the sheath or adherence of the prosthesis to the vessel is facilitated. To facilitate the introduction of the endoprosthesis into the sheath a mechanical device may be used. This device could consist of several parallel wires all connected to a ring. With the endoprosthesis placed between the wires, the ends of the wires are then inserted into the sheath. As the wires are advanced slowly into the sheath the prosthesis is gradually reduced in diameter and forced into the cannula. Another way to enfold the prosthesis, is in a foil or a membrane for easing introduction into the catheter or cannula. An additional technical aid which may be used is a friable non-toxic, thin cylinder or sleeve which can be placed around the prosthesis when it is collapsed over the balloon. The purpose of this sheath will be to keep the endoprosthesis in its collapsed psoition for introducing it into the cannula, and to facilitate movement into the sheath. As the endoprosthesis is delivered the thin fabric ruptures, permitting the endoprosthesis to resume its intended shape and diameter. Collogen, albumin or dissolvable suture material could be used for this purpose. Collogen and albumin remain strong enough to hold the sleeve until dissolved by body fluids. The endoprosthesis may be collapsed around the balloon catheter by wrapping it with a thread which is removed after the endoprosthesis is within the sheath, FIGS. 17 and 18. The thread is wrapped around the endoprosthesis with a reversal of direction on each turn, and a loop around a wire. When the wire is removed, the thread becomes loose, freeing the prosthesis and the thread. The thread is removed through the catheter. Lubrication may be used on the outside of the endoprosthesis to facilitate its movement through the sheath. Movement between the endoprosthesis and the balloon catheters is prevented by the way in which the endoprosthesis is compressed around the collapsing balloon.

The invention could be used in other applications. The invention could be designed to treat a weakened, damaged or stenotic urethra, ureter, esophagus, bile duct or the like.

The embodiments of the invention in which an exclusive property or privilege is claimed are defined as follows:

1. An apparatus for repairing a damaged area of a body vessel, comprising:

a resilient sleeve adapted for placement within the vessel and having a length sufficient to bridge the damaged area of said vessel, said sleeve being radially collapsible to a collapsed condition and capable of thereafter expanding to its original uncollapsed condition, said sleeve having an outside diameter sufficient to form an interference fit between the outer wall of the sleeve and the inner wall of the vessel throughout substantially the entire length of the sleeve;

percutaneous insertion means for inserting the sleeve into the body vessel, said insertion means including a thin walled sheath for retaining said sleeve in its collapsed condition against radially outward pressure exerted thereby during placement of said sleeve within said vessel, said insertion means being removable after placement of said sleeve within said vessel;

said thin walled sheath being provided at the end of an elongated flexible catheter adapted for percutaneous placement within said vessel for transporting said sleeve to the location of the damaged area of said vessel, said catheter and sheath being removable from said vessel while said sleeve is retained at the location of the damaged area of said vessel for allowing said sleeve to return to its original unexpanded condition upon withdrawal of said catheter and sheath; and collapsing means for collapsing said sleeve, comprising a thread adapted to be looped about the circumference of said sleeve throughout substantially the entire length of said sleeve, and to be tightened about said sleeve so as to collapse said sleeve onto said catheter for subsequent insertion of said sleeve into said thin walled sheath.

2. The apparatus according to claim 1, wherein said thread retains said sleeve in its collapsed condition prior to and during transport of said sleeve to the damaged area of said vessel, said thread being releasable upon placement of said sleeve thereat for allowing said sleeve to return to its original unexpanded condition to thereby bridge the damaged area of said vessel.

3. The apparatus according to claim 2, wherein said catheter is provided with an expandable balloon onto which said sleeve is collapsed, said expandable balloon acting to assist said sleeve in returning to its original unexpanded condition upon release of said thread from engagement with said sleeve.

4. The apparatus according to claim 1, wherein said collapsing means includes a longitudinally extending wire associated with said catheter, said wire being disposed exteriorly of said sleeve, and said thread adapted to be wrapped back and forth around said sleeve and said wire so that tightening of said thread causes said sleeve to collapse onto said catheter.

* * * * *